(12) United States Patent
Harkrider (10) Patent No.: US 6,682,542 B2
(45) Date of Patent: Jan. 27, 2004

(54) ENDOLUMINAL KNIFE

(76) Inventor: William W. Harkrider, 602 N. Lewis Ave., Suite 100, New Iberia, LA (US) 70563

( * ) Notice: Subject to any disclaimer, the term of this patent is extended or adjusted under 35 U.S.C. 154(b) by 219 days.

(21) Appl. No.: 09/733,995

(22) Filed: Dec. 12, 2000

(65) Prior Publication Data

US 2002/0072760 A1 Jun. 13, 2002

(51) Int. Cl.$^7$ .............................................. A61B 17/22
(52) U.S. Cl. ..................................... 606/159; 128/898
(58) Field of Search ......................... 606/159, 47, 171, 606/170, 167, 180; 30/287, 289; D24/147; 600/201, 210, 235, 562, 563, 564; 128/898; 604/222

(56) References Cited

U.S. PATENT DOCUMENTS

| | | | | |
|---|---|---|---|---|
| 769,829 A | * | 9/1904 | Mott | 606/171 |
| 2,180,457 A | * | 11/1939 | Butkiewicz | 30/240 |
| 2,202,085 A | * | 5/1940 | Brown | 30/276 |
| 3,937,222 A | * | 2/1976 | Banko | 606/170 |
| 3,945,117 A | * | 3/1976 | Beaver | 30/287 |
| 4,167,944 A | * | 9/1979 | Banko | 606/107 |
| 4,315,511 A | * | 2/1982 | Chin | 606/159 |
| 4,497,320 A | * | 2/1985 | Nicholson et al. | 606/79 |
| 4,559,927 A | * | 12/1985 | Chin | 128/898 |
| 4,621,636 A | * | 11/1986 | Fogarty | 606/159 |
| 4,674,503 A | * | 6/1987 | Peyman et al. | 606/166 |
| 4,707,920 A | * | 11/1987 | Montgomery | 30/294 |
| 4,790,312 A | * | 12/1988 | Capuano et al. | 606/171 |
| 4,887,598 A | * | 12/1989 | Berke | 606/180 |
| 4,887,599 A | * | 12/1989 | Muller | 606/180 |
| 4,899,742 A | * | 2/1990 | Muller | 606/180 |
| 5,078,724 A | * | 1/1992 | Takase | 606/167 |
| 5,112,339 A | * | 5/1992 | Zelman | 606/107 |
| 5,203,865 A | * | 4/1993 | Siepser | 606/166 |
| 5,211,651 A | * | 5/1993 | Reger et al. | 606/159 |
| 5,217,476 A | * | 6/1993 | Wishinsky | 606/167 |
| 5,234,436 A | * | 8/1993 | Eaton et al. | 606/107 |
| 5,250,064 A | * | 10/1993 | Schneider | 606/167 |
| 5,282,484 A | * | 2/1994 | Reger | 128/898 |
| 5,312,413 A | * | 5/1994 | Eaton et al. | 606/107 |

(List continued on next page.)

OTHER PUBLICATIONS

Queral et al., "Retrograde iliofemoral endarterectomy facilitated by balloon angioplasty", Dec. 1995, Journal of Vascular Surgery, pp. 742–750.

Ho et al., "The Mollring Cutter Remote Endarterectomy", 1995, Journal of Endovascular Surgery, pp. 2:278–287.

van der Heijden et al., "The cleavage plane in semi–closed endarterectomy of the superficial femoral artery: A Histologic Study", Oct. 1994, Journal of Vascular Surgery, pp. 607–612.

Hill, Bradley B., M.D., "Remote Endarterectomy and Stenting for SFA Occlusion", Stanford Vascular Symposium: Frontiers in Vascular Disease 1999, pp. 1–4.

Primary Examiner—John J. Calvert
Assistant Examiner—Alissa L. Hoey
(74) Attorney, Agent, or Firm—Duane Morris LLP (57) ABSTRACT

A device and method for cutting tissue to a precise depth in which a surgical blade with a rounded cutting edge, including a guard to limit the depth of penetration of the blade, is operatively connected to a handle. The device and method are particularly adapted to an endoluminal knife for cutting only the intima and media layers of a blood vessel wall during a endarterectomy procedure where the non-incised tissue is protected by the guard as the blade passes along the vessel to the point of incision. The angle of the blade may be fixed relative to the handle, or may be controllably varied by a movable cord catheter from an axial, non-contact position for the insertion and removal of the device into the artery to a radial or longitudinal, cutting position once the blade is in the desired location. Once the blade is embedded into the tissue, the device may be rotated by the handle, or by the rotation of the lumen or multilimenal catheter through which the knife has been inserted into the artery.

44 Claims, 3 Drawing Sheets

U.S. PATENT DOCUMENTS

| | | | | |
|---|---|---|---|---|
| 5,312,425 A | * | 5/1994 | Evans et al. | 606/159 |
| 5,338,292 A | * | 8/1994 | Clement et al. | 604/22 |
| 5,342,377 A | * | 8/1994 | Lazerson | 606/166 |
| 5,346,497 A | * | 9/1994 | Simon et al. | 606/107 |
| 5,370,652 A | * | 12/1994 | Kellan | 606/166 |
| 5,409,454 A | * | 4/1995 | Fischell et al. | 604/22 |
| 5,423,838 A | * | 6/1995 | Willard | 606/159 |
| 5,431,671 A | * | 7/1995 | Nallakrishnan | 606/167 |
| 5,522,829 A | * | 6/1996 | Michalos | 606/170 |
| 5,569,285 A | * | 10/1996 | Webb | 606/180 |
| 5,674,232 A | * | 10/1997 | Halliburton | 606/159 |
| 5,749,886 A | * | 5/1998 | Abidin et al. | 606/182 |
| 5,766,198 A | * | 6/1998 | Li | 606/172 |
| 5,769,865 A | * | 6/1998 | Kermode et al. | 606/167 |
| 5,769,866 A | * | 6/1998 | Frantzen | 606/167 |
| 5,820,629 A | * | 10/1998 | Cox | 606/159 |
| 5,824,057 A | * | 10/1998 | Plaia et al. | 128/898 |
| 5,843,102 A | * | 12/1998 | Kalmann et al. | 606/159 |
| 5,967,984 A | * | 10/1999 | Chu et al. | 600/439 |
| 6,027,514 A | * | 2/2000 | Stine et al. | 606/159 |
| 6,146,397 A | * | 11/2000 | Harkrider, Jr. | 606/159 |
| 6,165,187 A | * | 12/2000 | Reger | 606/159 |
| 6,241,745 B1 | * | 6/2001 | Rosenthal | 606/159 |
| 6,267,759 B1 | * | 7/2001 | Quick | 606/47 |
| 6,328,730 B1 | * | 12/2001 | Harkrider, Jr. | 604/523 |
| 6,363,617 B1 | * | 4/2002 | Frost | 30/370 |
| 6,438,850 B2 | * | 8/2002 | Young et al. | 30/162 |
| 6,484,407 B2 | * | 11/2002 | Khatchadourian et al. | 30/319 |

* cited by examiner

ENDOLUMINAL KNIFE

BACKGROUND OF THE INVENTION

This invention relates to a knife and surgical procedure where the depth of the incision is precisely limited.

It is known to provide surgical knives with an adjustable guard for limiting the depth of an incision. One such guard is described in the Beaver U.S. Pat. No. 3,945,117 dated Mar. 23, 1976, and comprises a plastic material which resiliently grips the blade. However, such guards are limited by their size and construction to incisions through the skin or other exposed surfaces and the depth of the incision may require great control over the angle at which the knife is held during the procedure, i.e., variation in the angle of the knife to the skin may significantly vary the dept of incision.

In one aspect, it is an object of the present invention to provide a novel knife and surgical method which obviates many of the problems associated with the use of guards on surgical knives, and which may be safely used in confined areas. Accordingly, it is an object of the present invention to provide a novel knife and method of making incisions of precise and easily controllable depth.

However, the present invention finds particular utility in making incisions within the confines of blood vessels, e.g., in the treatment of alterosclerosis by the removal of diseased tissue from an artery. As is well known, endarterectomy is the removal of the intimal and media layers of an artery from the inside of an artery leaving the radially outer adventitia layer intact as the conduit for the blood. A continuing problem with this long used medical procedure is that the withdrawal of the plaque from the artery may result in a "feathered" endpoint or flap at the point where the removal of tissue stops. Such flaps can limit blood flow and/or be thrombogenic. This possibility is reduced by the termination of the tissue and removal by an incision to provide a clear endpoint, i.e., a termination where all three layers remain attached to each other to thereby prevent blood flow between any two adjacent layers.

Figure 1:
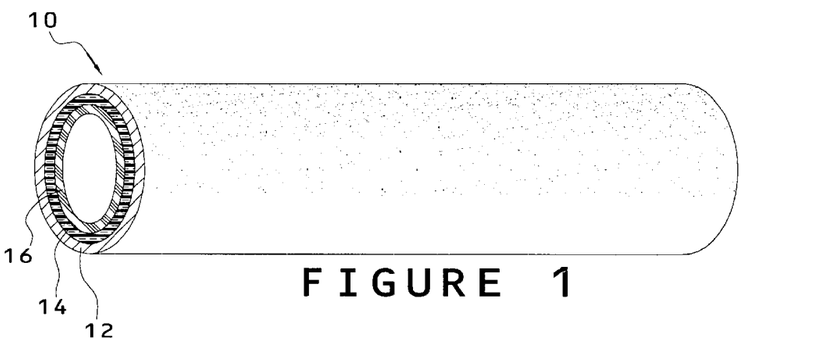
FIG. 1 is a pictorial view of an artery in cross-section showing the layers thereof.

As shown in cross-section in FIG. 1, an artery 10 is comprised of three layers, i.e., an outer layer or adventitia 12, a middle or media layer 14, and an intima-tunica or intimal lining 16. Deposits collect on the intimal wall and result in stenosis, blockage or complete obstruction of the flow of blood through the artery. The procedure for removal of a diseased intima and media layer from within the adventitia is known as an endarterectomy, and a new and healthy intima will grow from the adventitia. Devices for performing an endarterectomy are well known and an endarterectomy instrument and method are disclosed in U.S. patent application Ser. No. 09/286,653, entitled "ENDARTERECTOMY LOOP", filed Apr. 6, 1999, by the present inventor, the disclosure of which is hereby incorporated herein by reference.

The intima is a thin, several cell thick membrane which is not easily torn but which is readily separated from the media. The media comprises a much thicker layer of muscle cells circular in orientation and the adventitia is the layer which provides the strength of the artery. The media is easily separated from the adventitia and it these two radially inner layers, together with any associated plaque, which it is desirable to remove from the vessel. The media is generally separated from the outer wall by a ring stripper for some axial distance upstream of the endpoint where the media and intima are to be severed. Once the diseased tissue is loosened from the adventia, the diseased tissue may be removed from the vessel.

Figure 2:
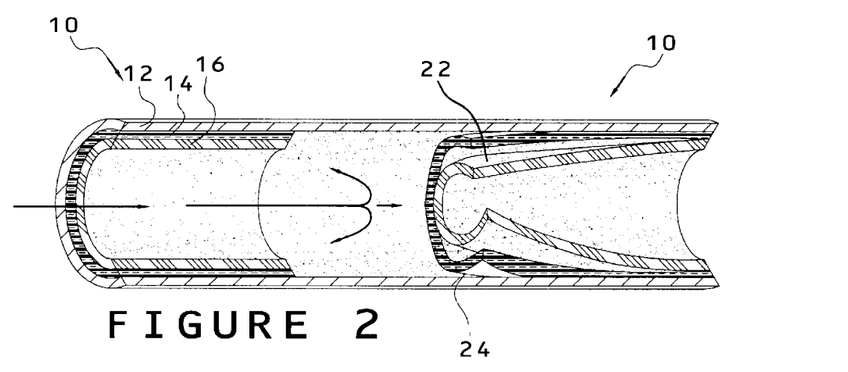
FIG. 2 is a pictorial view of an artery in longitudinal section with an endarterectomized portion of the artery showing an endpoint with flap formation by separation of the intima from the media and by separation of the media and intima from the adventitia.
Figure 3:
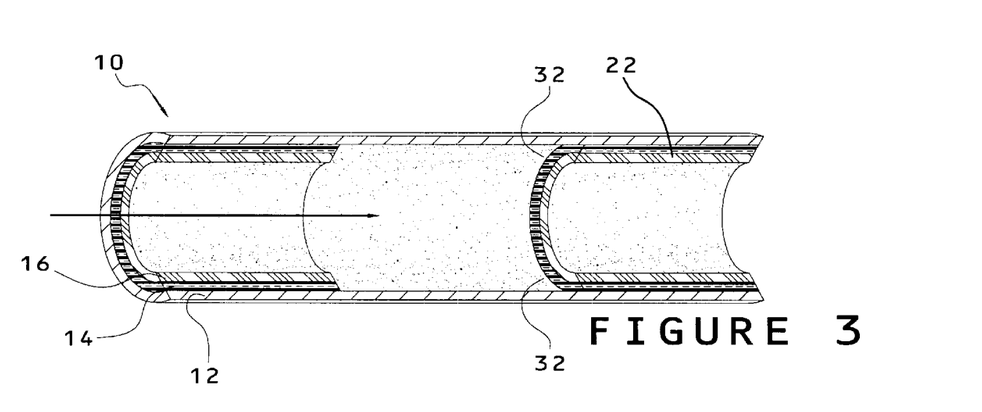
FIG. 3 is a pictorial view of an artery in longitudinal section with an endarterectomized portion of the artery showing a clear endpoint where the three sections of the artery remain attached.

As shown in FIG. 2, a feathered endpoint may be formed if all three layers do not remain attached to each other. Separation of the layers from each other at the endpoint may result in the formation of a flap 22 between the media 14 and intima 12 or a flap 24 between the adventitia 16 and the media 14 and intima 12. Such a flap 22, 24 in the artery 10 may be flow limiting and/or thrombogenic in nature. FIG. 3 shows a clear endpoint 32 formed in an artery 10 by the use of the present invention.

It is known to address this intima flap problem by vascular stents, but such stents are expensive and reduce the flexibility of the vessel. An alternative is described in the Cox U.S. Pat. No. 5,820,629 dated Oct. 13, 1998, in which a smooth transition in the intimal lining is attempted by an electrocautery coil or a radially extending blade which is inserted down the artery beyond the area of separation of the media, expanded, and then withdrawn to effect cutting of the intima and media. This procedure requires the mechanical operation of the device within the artery and great precision in the angling of the blades and depth of insertion to effect the meeting of the point of separation of the media from the adventitia at the end of the angled cut.

The risk of separation of the three layers is significantly reduced by cutting the media and intima together. It is accordingly an object of the present invention to provide an endarterectomy knife and method which obviates many of the deficiencies of known devices and methods for cutting of the intima and media layers of a blood vessel wall.

It is another object of the present invention to provide a novel device and method in which the blade is shielded from contact with the vessel during insertion and removal thereof and exposed only for the surgical procedure.

It is still another object of the present invention to provide a novel hand held device and method in which the blade is shielded from contact with the vessel during insertion and removal thereof and exposed for the surgical procedure by the angulation of the shaft relative to the vessel or the rotation of the blade relative to the shaft.

These and many other objects and advantages of the present invention will be readily apparent to one skilled in the art to which the invention pertains from a perusal of the claims, the appended drawings, and the following detailed description of the preferred embodiments.

DESCRIPTION OF PREFERRED EMBODIMENTS

Figure 4A:
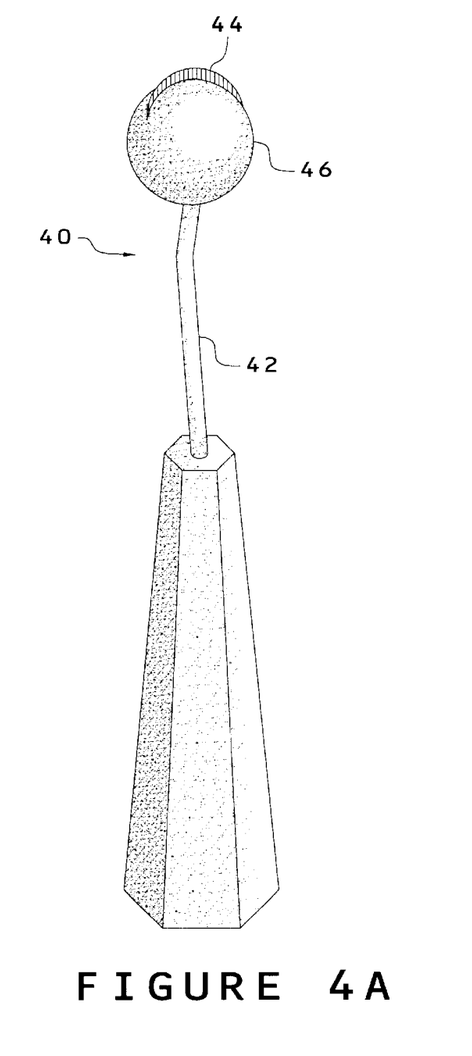
FIGS. 4(a) and 4(b) are a pictorial view of a first embodiment of the endoluminal knife of the present invention with the position of the blade and its protective housing fixed relative to the shaft.
Figure 4B:
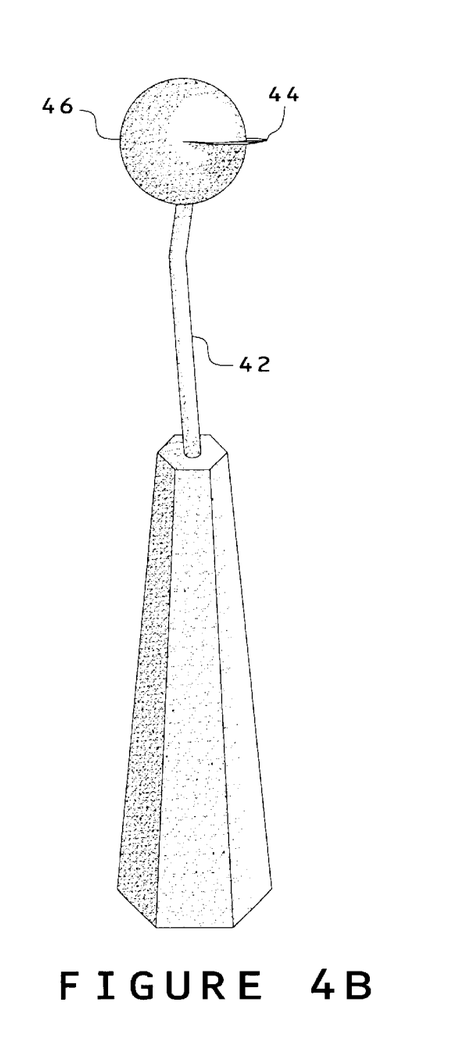

FIG. 4 illustrates one embodiment of the present invention. Referring to FIG. 4, the device 40 may be used for cutting only the intima and media layers of a blood vessel wall during a endarterectomy procedure without forming a flap of the intimal and media layers which could potentially obstruct the flow of blood through the vessel. The device 40 may comprise a handle 42, surgical blade 44, and guard 46.

The handle 42 may be suitable for gripping by the hand of a physician externally of the blood vessel. The handle 42 may be any suitable material and is desirably comprised of bendable material, e.g., the handle 42 may be a wire coil with coated plastic or the handle 42 may be made of material similar to biopsy forceps. The handle 42 may be fairly stiff to retain its shape while in use and may allow for axial rotation with close to a one-to-one ratio.

The handle 42 may include ridges or serration grooves to allow for a better grip of the handle 42 by the physician. The length of the handle 42 may vary from about 5 cm to about 20 cm. The handle 42 may be malleable so that the handle 42 may be angled or adjusted nearest the guard 46 to allow the physician to determine the angle of approach of the blade 44 to the vessel wall.

The surgical blade 44 may be operatively connected to the handle 42 by any suitable means or the blade 42 and handle 44 may be a unitary structure. The blade 44 may be stainless steel or may be an alloy, and may be rounded or arcuate so that the blade 44 may gradually engage the surface to be cut. The blade 44 may be generally arcuate with a radius approximating the radius of the guard 46 so that the exit of the cutting edge from the guard 46 may be generally tangential to the outer surface of the guard 46 at both ends of the cutting edge.

The cutting edge of the blade 44 is desirably smooth and extremely sharp. The length of the cutting edge of the blade 44 may be substantially greater than the maximum distance from the cutting edge to the guard 46. The distance from the cutting edge of the blade 44 to the guard 46 may range between about 0.1 mm and 2.0 mm. The ratio of the length of the cutting edge of the blade 44 to the maximum distance from the cutting edge to the guard 46 may be not less than about 3, and may be about 5.

The guard 46 may be any suitable inert material, e.g., nonreactive plastic or hydrophilic plastic. The guard 46 may be any suitable shape, e.g., a perfect sphere, generally spherical or ellipsoidal. The size of the guard 46 may be chosen by the physician to hold the wall of the vessel open during the rotation of the device 40, to minimize trauma to the artery, and/or to minimize the risk of the blade 44 contacting the vessel wall as the blade 44 passes within the vessel. The ratio of the diameter of the guard to the diameter of the vessel may range between 0.2 and 1. When the guard is generally spherical, for example, the ratio of the radius of the cutting edge of the blade 44 to the radius of the guard 46 may range between about 0.8 and 1.2. A device 40 having a guard diameter of 1 mm may be used with a vessel with a 4 mm diameter or a 20 mm diameter.

The physician may choose the configuration of the device 40 or device 60 (as shown in FIG. 5) to be used in the endarterectomy procedure based on the a variety of factors, e.g., the size of the vessel, the location of the vessel within the body, and the location of the diseased tissue within the vessel. The possible configurations of the device 40, 60 may vary based on (1) the size and shape of the guard 44, 64; (2) the size and shape of the blade 46, 66; (3) the length of the handle 42, 62; and (4) the angle between the handle 42, 62 and the blade 46, 66.

Referring again to FIG. 4, the device 40 may be used by the physician to perform an endarterectomy procedure from a single incision point transverse to the longitudinal axis of the blood vessel. The vessel may be exposed by conventional methods and then an incision may be made from the exterior of the vessel wall to obtain an entry point for the device 40 into the vessel. The physician may choose the device 40 to perform the endarterectomy as described herein. The physician may then manually adjust the angle of the handle 42 to set the angle at which the blade 44 may engage the vessel wall, e.g., approximately 90° to the longitudinal axis of the vessel.

The device 40 may then be inserted into the vessel via the incision point and the handle 42 may be pushed by the physician to position the blade 44 and guard 46 along the longitudinal axis of the vessel up to the location of the endpoint. Often times the physician utilizes a conventional high intensity light to illuminate the vessel and to show the position of the blade 44 within the vessel. The device 40 may be pushed in a manner to avoid contact between the blade 44 and the vessel wall. A lumen may also be inserted within the vessel up to the point where the endpoint may be cut and the device 40 inserted therein.

When the blade 44 is properly positioned within the vessel, the physician may manipulate the handle 42 to allow the blade 44 to gradually embed itself into the vessel wall. The blade 44 may penetrate the vessel wall through the intima and media layers with the guard 46 preventing the blade 44 from entering the adventia layer. Once the blade 44 has penetrated the vessel wall, the physician may rotate the handle 42 through 360°, which in turn causes the blade 44 to circumferentially cut the intima and media layers to form a clean endpoint. The physician may then manipulate the handle 42 to remove the blade 44 from the vessel wall, and may then remove the device 40 from the vessel by pulling the handle 42 while keeping the blade 44 from contacting the vessel wall.

The diseased intima and media layers of the vessel may be then loosened from the adventia up to the endpoint by any suitable means, e.g., endarterectomy loop or ring stripper. The instrument described in the Harkrider U.S. Pat. No. 6,146, 397 dated Nov. 14, 2000, for an ENDARTERECTOMY LOOP may be suitable. The loosened diseased layers may then be removed by any suitable means, e.g., suction or clamp. After the diseased layers are removed, the vessel incision may be closed.

The device 40 may also be used by the physician to perform an endarterectomy from an incision point made along the length of the artery or vessel. The physician may gain access to the exposed artery by making a longitudinal incision through the blood vessel wall from the exterior of the artery. The longitudinal incision will cause the artery to lay in a flat open position exposing the interior of the artery. The physician may choose the device 40 to perform the endarterectomy as described herein.

The physician may then utilize the device 40 to make a first and second transverse cut through the intima and media layers of the artery nearest the ends of the longitudinal incision which will result in the formation of two clear endpoints. After the two cuts are made into the exposed artery, the physician may use the blade 44 to peel the intimal and media layers from the adventia layer. The physician may also make additional longitudinal or transverse cuts into the artery wall, as needed, to facilitate the peeling of the intima and media layers from the artery wall. The intima and media layers may be completely peeled from the adventia between the two endpoints and completely removed from the artery wall. Once the diseased inner layers are removed the artery may be closed.

Figure 5A:
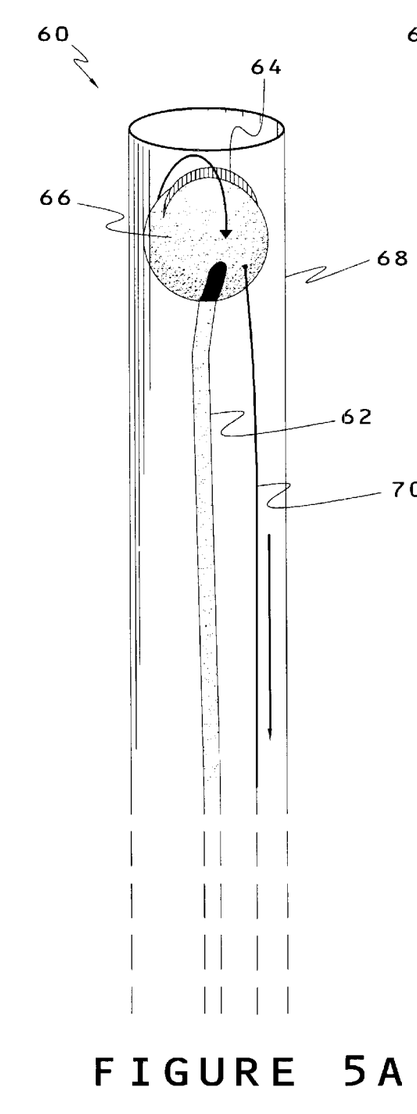
FIG. 5 is a pictorial view of a second embodiment of the endoluminal knife of the present invention with the position of the blade and its protective housing movable relative to the shaft from the insertion and removal position of FIG. 5(a) to the cutting position of FIG. 5(b).
Figure 5B:
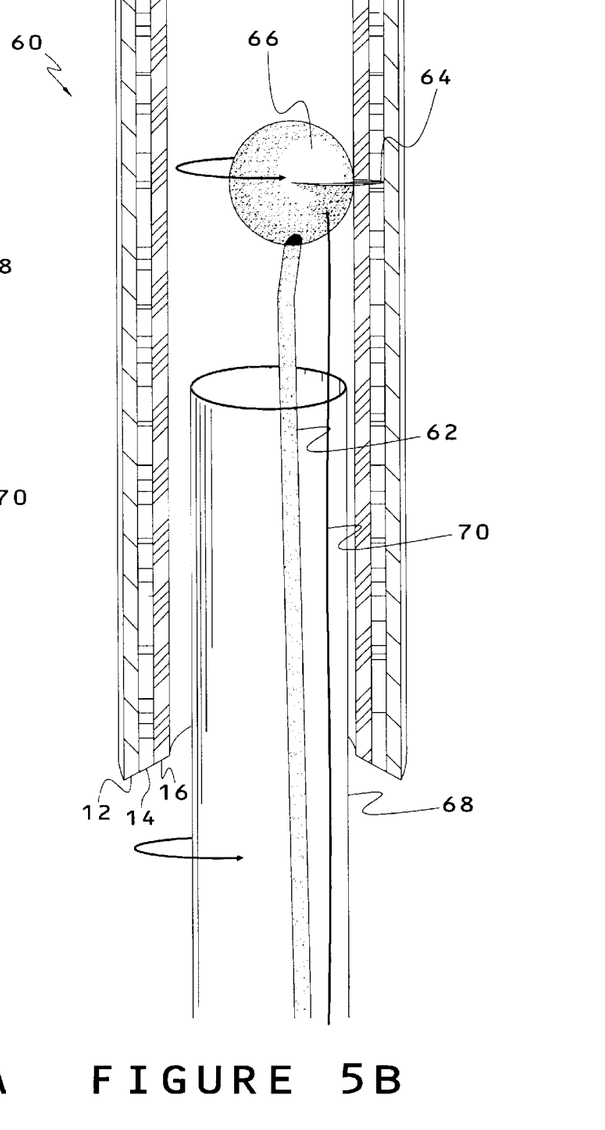

FIG. 5 illustrates another embodiment of the present invention. Referring to FIGS. 5(a) and 5(b), the device 60 may be used in an endarterectomy procedure and may be operated through the lumen of a catheter 68 to cut the intima and media layers of a blood vessel without severing the adventia of the blood vessel. The device 60 may also be used within the vessel without a catheter 68 or within a multilumen catheter. The device 60 may comprise an elongated handle 62, blade 64, guard 66 and a means to pivot the guard 66 to rotate the blade 64 from a first position to a second position within the vessel.

The guard 66 may be pivotally carried by the handle 62 and the device 60 may include a means for pivoting the guard 66 from the proximate end of the handle 62 so that the blade 64 may be rotated from a first position facing along the axis of the vessel to a second position. The guard 66 may be pivotably carried by the handle 62 by any suitable means, e.g., pin, bolt, or ball joint. The length of handle 62 may vary from 5 cm to 100 cm or longer as needed depending on the procedure to be performed. The guard 66 may be pivoted by any suitable means, e.g., a wire 70 connected to the guard 66 or two wires connected to the guard 66. The wire 70 may be sufficiently rigid to allow the physician to manipulate the wire to push or pull the guard 66 and blade 64 into position. The device 60 may also include a latch 72 for selectively maintaining the position of the guard 66 and blade 64. The latch 72 may be any suitable means, e.g., locking screw, ratchet and handle, or locking nut.

The guard 66 may be pivoted from the proximate end of the handle 62 by a wire 70 in order to rotate the blade 64 from a first position facing forwardly along the axis of the vessel to a second position. The second position may be either facing transversely to the axis of the vessel or facing longitudinal to the axis of the vessel. In yet another embodiment of the invention, the device 60 may include 2 wires which may be attached to the guard 66, so that the guard 66 and blade 64 may be pivoted from the proximate end of the handle 62 from a first wire so that the blade 64 may be rotated from a first position facing forwardly along the axis of the vessel to a second position facing transversely to the axis of the vessel or rotated by a second wire so that the blade 64 may be rotated to a third position facing longitudinal to the axis of the vessel.

Referring again to FIGS. 5(a) and (b), the device 60 may be used within the lumen of a catheter 68 to perform an endarterectomy procedure. The physician may first insert a catheter 68 into the artery. The physician will normally view the diseased tissue within the artery by first inserting optics within the lumen of the catheter 68 and viewing the diseased tissue to determine where to locate the endpoints.

The device 60 may then be inserted into the lumen of the catheter 68 with the blade 64 facing forward along the longitudinal axis of the vessel. The position of the blade 64 facing forward allows the blade 64 to pass through the catheter 68 without damaging the catheter 68 wall. Once the blade 64 exits the catheter 68, the physician may rotate the blade 64 by pushing or pulling the wire 70 to change the orientation of the blade 64 from facing forward along the longitudinal axis of the vessel to facing transversely to the longitudinal axis of the vessel. The wire 70 may then be locked in place by the latch 72 to position the blade 64 at the endpoint location.

The handle 62 may then be manipulated by the physician to allow the blade 64 to gradually embed into the vessel wall as shown in FIG. 5(b). The blade 64 may penetrate the vessel wall through the intima 16 and media 14 layers. The guard 66 prevents the blade 64 from entering the adventia 12 layer. Once the blade 64 has penetrated the vessel wall, the physician may rotate the catheter 68 through 360° which in turn causes the blade 64 to circumferentially cut the intima 16 and media 14 layers to form a clean endpoint. The physician may then manipulate the handle 62 to remove the blade 64 from the vessel wall and face the blade 64 away from the vessel wall. The wire 70 may then be pushed to position the blade 64 to face forward and the handle 62 may be pulled to return the blade back within the lumen of the catheter 68.

After the first endpoint is cut, the physician may remove the catheter 68 a predetermined distance to position the end of the catheter 68 at the location of the second endpoint. These same steps used in cutting the first endpoint are repeated to establish a second endpoint. The physician may then again rotate the blade 64 back into a position facing forward along the longitudinal axis of the vessel and pull the blade 64 back into the lumen of the catheter 68. The device 60 may then be removed from the catheter 68. In some instances the physician may not cut a second endpoint.

After the device 60 is removed from the catheter, the diseased tissue may be loosened from the adventia between the two endpoints, or up to the single endpoint, by any suitable means, e.g., endarterectomy loop or ring stripper. For example, the physician may insert an endarterectomy loop into the catheter 68 to loosen the diseased tissue from the adventia 12 layer between the first and second endpoints. After the diseased tissue is loosened from the adventia 12 layer, the diseased tissue may then be removed through the catheter 68 by any suitable means, e.g., suction. Once the diseased tissue is removed, the catheter 68 may be removed from the vessel.

Referring again to FIG. 5, the device 60 may also be used within a multilumen catheter to perform an endarterectomy. The instrument described in the Harkrider U.S. patent application Ser. No. 09/276,679 for ENDOLUMINAL MULTI-LUMINAL SURGICAL SHEATH AND METHOD is a suitable catheter.

An exterior incision may be made in the vessel and the multilumen catheter may be inserted into the vessel. The physician may then insert optics into the first lumen of the catheter for viewing and to thereby locate the diseased tissue. The physician may choose the device 60 to perform the endarterectomy as described herein. The physician may then position multilumen catheter to a position adjacent the location of the first endpoint.

The physician may then insert the device 60 into a second lumen of the multilumen catheter with the blade 64 facing forward along the longitudinal axis of the vessel. The blade 64 and guard 66 may be pushed by the handle 62 within the second lumen until the blade 64 and guard 66 exit the second lumen as viewed by the physician through the optics in the first lumen.

The blade 64 may then be rotated about the pivot point of the handle 62 by pulling the wire 70 to change the orientation of the blade 64 from facing forward along the longitudinal axis of the vessel to facing transversely to the longitudinal axis of the vessel. The position of the guard 66 and blade 64 may then be locked by latch 72 at the position of the second endpoint location. The position may be latched by any suitable means, e.g., locking screw, ratchet and handle, or locking nut.

The handle 62 may then be manipulated to allow the blade 64 to gradually embed into the vessel wall. The blade 64 may penetrate the vessel wall through the intima and media layers. The guard 66 prevents the blade 64 from entering the adventia layer. Once the blade 64 has penetrated the vessel wall, the physician may rotate the multilumen catheter 360° which in turn causes the blade 44 to circumferentially cut the intima and media layers to form a clear endpoint. The physician may then manipulate the handle 62 to remove the blade 64 from the vessel wall and face the blade 64 away from the vessel wall.

After the first endpoint is established the physician may remove the multilumen catheter a predetermined distance to the location of the second endpoint. These same steps used in cutting the first endpoint are repeated to establish a second endpoint. The physician may then manipulate the handle 62 to remove the blade 64 from the vessel wall and to face the blade 64 away from the vessel wall. The latch 72 may be released and the wire 70 may be pushed to position the blade forward along the longitudinal axis of the vessel and the device 60 may then be removed from the multilumen catheter. The physician may then loosen the diseased tissue between the two endpoints or up to a single endpoint. For example, the physician may insert an endarterectomy loop to loosen the diseased tissue from the adventia layer. Once the diseased tissue is loosened from the vessel wall, the diseased tissue may be removed through a lumen of the multilumen catheter by any suitable means e.g., suction or by inserting a clamping device into the multilumen catheter. Once the diseased tissue is removed, the multilumen catheter may be removed from the vessel.

The device 60 may also be used to cut the vessel wall in a longitudinal direction. After the blade 64 exits the catheter 68 or multilumen catheter the blade 64 may be rotated from a position facing forward along the longitudinal axis of the vessel to a position longitudinal to the vessel and the blade 64 may be embedded into the vessel wall. The catheter 68 or multilumen catheter may then be pulled or pushed to cut longitudinal incisions into the vessel. The blade 64 may then be rotated back to a position where the blade 64 faces forward along the longitudinal axis of the vessel.

In another embodiment of the invention the device 60 may also include two wires which may rotate the blade 64 in two different directions, i.e., longitudinally and transversely, so that the endpoint and longitudinal incisions may be made by only one device 60 within the vessel. A wire 70 may be used to position the blade 64 transversely to the axis of the vessel and a wire 74 (not shown) may be used to position the blade longitudinally to the axis of the vessel.

While preferred embodiments of the present invention have been described, it is to be understood that the embodiments described are illustrative only and the scope of the invention is to be defined solely by the appended claims when accorded a full range of equivalence, many variations and modifications naturally occurring to those of skill in the art from a perusal hereof.

What is claimed is:

1. A device for severing from the interior of a blood vessel (a) a portion of the intimal and media layers to be separated from the adventitia of the blood vessel from (b) portions of the intimal and media layers which are to remain attached to the adventitia of the blood vessel, without forming a flap of the intimal and media layers which could potentially obstruct the flow of blood through the vessel, said device comprising:
    a handle suitable for gripping by the hand of a physician externally of the vessel;
    a surgical blade operatively connected to said handle and being suitable for insertion into a vessel to be manipulated therein by the manipulation of said handle by the physician, said blade having a rounded cutting edge; and
    a guard for limiting the depth of any incision made by said blade to the thickness of the intimal and media layers of the vessel.

2. The device of claim 1 wherein said guard is generally spherical.

3. The device of claim 2 wherein said cutting edge is generally arcuate with a radius approximating the radius of said guard so that the exit of said cutting edge from said guard is generally tangential to the outer surface of said guard at both ends of said edge.

4. The device of claim 1 wherein the length of said cutting edge is substantially greater than the maximum distance from said cutting edge to said guard.

5. The device of claim 4 wherein the ratio of the length of said cutting edge to said maximum distance is not less than about 3.

6. The device of claim 4 wherein the maximum distance from said cutting edge to said guard is between about 0.1 mm and 2.0 mm.

7. The device of claim 1 wherein said blade faces a direction at an angle to the axis of said handle to thereby facilitate insertion of said blade into the vessel without contact therewith and the subsequent movement of said blade into contact with the vessel by movement of said handle.

8. The device of claim 7 wherein the angle between the blade and the handle is selectively variable by the physician.

9. The device of claim 1 wherein the ratio of the diameter of said guard to the diameter of the vessel is about 0.2.

10. The device of claim 9 wherein said blade faces approximately 90° to the longitudinal axis of the vessel when inserted therein.

11. The device of claim 1 wherein the extension of said blade from said guard is a maximum at the midpoint of the exposed cutting edge and gradually reduces to both ends of the cutting edge.

12. A device for severing from the interior of a blood vessel the intimal and media layers of the blood vessel without severing the adventitia of the blood vessel comprising:
    a handle suitable for gripping by the hand of a physician externally of the vessel;
    a surgical blade with an arcuate cutting edge operatively connected to said handle and being suitable for insertion into a vessel; and
    a guard for limiting the depth of any incision made by said blade from the interior of the vessel.

13. The device of claim 12 wherein said guard is generally spherical; and
    wherein ratio of the radius of said cutting edge to the radius of said guard is between about 0.8 and about 1.2.

14. The device of claim 12 wherein said guard is generally spherical; and
    wherein ratio of the diameters of said guard and the vessel is less than about 0.5.

15. The device of claim 12 wherein the angle between the direction in which said blade faces and the axis of the handle is selectively variable by the physician.

16. In a hand held surgical knife for operating within the interior of a blood vessel, the improvement wherein the exposed cutting edge of the blade is generally arcuate over the entire exposed area of the blade.

17. In a hand held surgical knife for operating within the interior of a blood vessel, the improvement wherein the exposure of the cutting edge of the blade is limited by a generally spherical guard.

18. The knife of claim 17 wherein the ratio of the diameters of said generally spherical guard and the vessel is between about 0.2 and about 0.6.

19. A device for operating through a lumen in a catheter on the intimal and media layers of the blood vessel without severing the adventitia of the blood vessel comprising:
- an elongated handle having a distal end adapted for insertion through a first lumen of a catheter into a blood vessel;
- a blade with an elongated cutting edge;
- a guard carrying said blade and being pivotably carried by said handle at the distal end thereof, said guard limiting the depth of any incision made by said blade to the thickness of the intima and media layers of the vessel; and
- means for pivoting said guard from the proximate end of said handle so that said blade may be rotated from a first position facing forwardly along the axis of the vessel to a second position facing transversely to the axis of the vessel.

20. The device of claim 19 wherein said pivoting means includes a wire connected to said guard; and
- wherein the cutting edge of said blade is longitudinal to the axis of the vessel when said blade is in said second position.

21. The device of claim 20 wherein said wire is sufficiently rigid to push said blade back to said first position.

22. The device of claim 20 wherein said pivoting means further includes a wire connected to said guard for pulling said blade back to said first position.

23. The device of claim 19 wherein said pivoting means includes a wire connected to said guard; and
- wherein the cutting edge of said blade is transverse to the axis of the vessel when said blade is in said second position.

24. The device of claim 23 wherein said wire is sufficiently rigid to push said blade back to said first position.

25. The device of claim 23 wherein said pivoting means further includes a wire connected to said guard for pulling said blade back to said first position.

26. The device of claim 25 wherein said wire is sufficiently rigid to push said blade back to said first position.

27. The device of claim 19 wherein said guard is grooved over the proximate half thereof and is pivotably carried by said handle by a ball joint; and
- wherein said device includes a first wire for pivoting the cutting edge of said blade longitudinal to the vessel, and a second wire for pivoting the cutting edge of said blade transverse to the vessel.

28. The device of claim 19 including a latch for selectively maintaining the position of said guard.

29. The device of claim 19 wherein said guard is rotatable about the axis of the vessel by the rotation of said handle with respect to the vessel.

30. The device of claim 19 wherein said guard is rotatable about the axis of the vessel by the rotation of said catheter with respect to the vessel.

31. A system for performing incisions in the interior wall of a blood vessel comprising:
- a multilumen catheter adapted for insertion into a blood vessel;
- an optical device selectively positionable into the blood vessel through a first lumen in said catheter; and
- a knife selectively positionable into the blood vessel through a second lumen in said catheter, said knife having a cutting edge selectively positionable from the proximate end of said catheter relative to the axis of said second lumen into a first position facilitating the passage of said knife through said second lumen without damage to said catheter and into a second position facing and in contact with the interior wall of the vessel so that movement of said catheter relative to the vessel will effect an incision in the vessel wall.

32. The system of claim 31 wherein the cutting edge of said blade is transverse to the catheter when in said second position so that rotation of said catheter will effect a transverse incision in the vessel wall.

33. The system of claim 31 wherein the cutting edge of said blade is longitudinal to the catheter when in said second position so that longitudinal movement of the catheter relative to the vessel will effect a longitudinal incision in the vessel wall.

34. The system of claim 31 wherein the cutting edge of said blade is longitudinal to the catheter when in said second position so that longitudinal movement of the knife relative to the vessel will effect a longitudinal incision in the vessel wall.

35. The system of claim 31 including a guard for said knife to limit the depth of the incision and thereby prevent the severing of the adventitia of the vessel.

36. The system of claim 35 wherein said guard is generally spherical.

37. The system of claim 31 wherein said knife has an arcuate cutting edge.

38. A method of severing from the interior of a blood vessel (a) a portion of the intimal and media layers to be separated from the adventitia of the blood vessel from (b) portions of the intimal and media layers which are to remain attached to the adventitia of the blood vessel, without forming a flap of the intimal and media layers which could potentially obstruct the flow of blood through the vessel, comprising the steps of:
- (a) providing a surgical knife having a handle and a blade with a guard for limiting the depth of any incision made by said blade to the thickness of the intimal and media layers of the vessel;
- (b) inserting the blade into the vessel with the blade facing forwardly along the longitudinal axis of the vessel to the position in the vessel at which an incision is desired; and
- (c) manipulating the handle of the knife outside of the vessel to thereby cause the blade to incise the adjacent wall of the vessel with the depth of the incision progressing as the blade is manipulated.

39. A method of removing the intimal and media layers from a blood vessel comprising the steps of:
- (a) providing a knife having a blade, a handle and a guard for selectively limiting the depth of any incision by the blade;
- (b) making a longitudinal incision through the blood vessel wall from the exterior thereof to thereby obtain an entry for the knife into the blood vessel;
- (c) adjusting the exposure of the blade by the guard to thereby limit the depth of any incision made by the blade to the combined thickness of the intima and media layers of the vessel;
- (d) making incisions of the intima and media layers transverse to the longitudinal axis of the vessel from the interior of the vessel at two spaced apart locations along the length of the vessel;

(e) separating the intima and media layers from the adventitia of the vessel between the two incisions;

(f) removing the separated layers from the vessel; and (g) closing the longitudinal incision.

40. A method of severing from the interior of a blood vessel (a) a portion of the intima and media layers to be separated from the adventitia of the blood vessel from (b) portions of the intimal and media layers which are to remain attached to the adventitia of the blood vessel, without forming a flap of the intima and media layers which could potentially obstruct the flow of blood through the vessel, comprising the steps of:

(a) inserting a multilumen catheter into a blood vessel;

(b) inserting an optical device into the blood vessel through a first lumen of the catheter to thereby locate the desired place for an incision relative to the separated layers;

(c) providing a knife having a blade, a handle, pivoting means, and a guard for selectively limiting the depth of any incision by the blade;

(d) adjusting the exposure of the blade by the guard to thereby limit the depth of any incision made by the blade to the combined thickness of the intima and media layers of the vessel;

(e) inserting the blade into the vessel through a second lumen of the catheter with the blade facing forwardly along the longitudinal axis of the vessel and positioning the blade in the vessel at the location in which an incision is desired;

(f) manipulating the orientation of the blade with respect to the vessel from the proximate end of the catheter to thereby cause the blade to face and then enter the adjacent wall of the vessel; and (g) moving the catheter with respect to the vessel to thereby cause the blade to incise the intima and media layers of the vessel.

41. A method of removing lining from a blood vessel wall that reduces formation of a flap of lining extending into the vessel to interfere with blood flow comprising the following steps:

(a) providing a cutting tool with a curved surgical blade protruding out of a substantially spherical guard;

(b) adjusting the amount of the blade protruding out of the guard;

(c) separating a section of lining from a blood vessel wall from a beginning point to an endpoint;

(d) inserting a protective lumen into the blood vessel;

(e) inserting the knife into protective lumen;

(f) extending the blade of the knife out of the distal end of the protective lumen so that the blade engages the vessel wall adjacent the end point;

(g) rotating the knife within the blood vessel to thereby cleanly cut the the lining at the end point without forming a flap and so that contact between the guard and the lining limits the depth of the cut;

(h) removing the knife from the lumen; and (i) removing the separated lining from the blood vessel.

42. The device of claim 1, further comprising:

a multilumen catheter adapted for insertion into the blood vessel;

an optical device selectively positionable into the blood vessel through a first lumen in said catheter; and said blade selectively positionable into the blood vessel through a second lumen in said catheter, said blade having a cutting edge selectively positionable from the proximate end of said catheter relative to the axis of said second lumen into a first position facilitating the passage of said blade through said second lumen without damage to said catheter and into a second position facing and in contact with the interior wall of the vessel so that movement of said catheter relative to the vessel will effect an incision in the vessel wall.

43. The device of claim 42, wherein the cutting edge of said blade is transverse to the catheter when in said second position so that rotation of said catheter will effect a transverse incision in the vessel wall.

44. The device of claim 42 wherein the cutting edge of said blade is longitudinal to the catheter when in said second position so that longitudinal movement of the catheter relative to the vessel will effect a longitudinal incision in the vessel wall.

* * * * *